(12) United States Patent
Olivo et al.

(10) Patent No.: US 7,869,567 B2
(45) Date of Patent: Jan. 11, 2011

(54) PHASE CONTRAST IMAGING

(75) Inventors: Alessandro Olivo, London (GB);
Robert D. Speller, Cheddington (GB)

(73) Assignee: UCL Business PLC (GB)

( * ) Notice: Subject to any disclaimer, the term of this patent is extended or adjusted under 35 U.S.C. 154(b) by 2 days.

(21) Appl. No.: 12/439,742

(22) PCT Filed: Sep. 3, 2007

(86) PCT No.: PCT/GB2007/003318

§ 371 (c)(1),
(2), (4) Date: May 29, 2009

(87) PCT Pub. No.: WO2008/029107

PCT Pub. Date: Mar. 13, 2008

(65) Prior Publication Data

US 2010/0054415 A1    Mar. 4, 2010

(30) Foreign Application Priority Data

Sep. 8, 2006    (GB) .................................. 0617637.4

(51) Int. Cl.
*G01N 23/20* (2006.01)
(52) U.S. Cl. .............................. 378/87; 378/62; 378/70
(58) Field of Classification Search .................. 378/62, 378/70, 87
See application file for complete search history.

(56) References Cited

U.S. PATENT DOCUMENTS

| | | | |
|---|---|---|---|
| 3,944,833 A | | 3/1976 | Hounsfield |
| 5,684,851 A | * | 11/1997 | Kurbatov et al. ............... 378/87 |
| 5,802,137 A | | 9/1998 | Wilkins |
| 5,812,629 A | * | 9/1998 | Clauser ......................... 378/62 |
| 6,175,117 B1 | * | 1/2001 | Komardin et al. ........ 250/363.06 |
| 7,412,026 B2 | * | 8/2008 | Liu et al. ........................ 378/62 |
| 2003/0123611 A1 | | 7/2003 | Ohara |
| 2006/0039532 A1 | | 2/2006 | Wu |

OTHER PUBLICATIONS

Olivo, "An innovative digital imaging set-up allowing . . . ", Medical Physics, vol. 28, No. 8, Aug. 2001, pp. 1610-1619.
Pfeiffer, "Phase retrieval and differential phase-contrast . . . ", Nature Physics, vol. 2, No. 4, Apr. 2006, pp. 258-261.

* cited by examiner

*Primary Examiner*—Edward J Glick
*Assistant Examiner*—Thomas R Artman
(74) *Attorney, Agent, or Firm*—Barnes & Thornburg LLP

(57) ABSTRACT

Phase contrast imaging is achieved using a sample mask 8 and a detector mask (6). X-rays emitted from x-ray source (2) are formed into individual beams (16) by sample mask which pass through sample (14) and arrive at individual pixels (12) of the detector (4) through detector mask (6). The individual x-ray beams are arranged to hit the pixel edge (20) of individual rows of pixels, individual columns of pixels or individual pixels. Small deviations θ in the individual beams (16) cause a significant increase or decrease in the signal hitting the exposed area (22) of the pixel resulting in a significant phase contrast signal.

21 Claims, 8 Drawing Sheets

PHASE CONTRAST IMAGING

FIELD OF INVENTION

The invention consists in an apparatus for generating a phase contrast (PC) x-ray image and a method of generating such an image.

BACKGROUND ART

Phase contrast (PC) is an exciting emerging x-ray imaging technique which removes most of the limitations of conventional x-ray imaging. Phase contrast can be applied to all fields of x-ray imaging, i.e. medical (diagnosis and treatment planning/delivering/monitoring), industrial (inspections, non-destructive testing) as well as to homeland security (security inspections). Basically all these fields would strongly benefit from the introduction of a reliable PC technique, as this would result in a strongly increased visibility of all details and in the possibility of detecting features which are invisible to conventional techniques.

A review of PC imaging is provided in R. Lewis, Medical phase contrast x-ray imaging: current status and future prospects, Phys. Med. Biol. volume 49 (2004) pages 3573-83.

Unlike more conventional techniques, which are based on absorption, PC is based on phase shift effects. The term responsible for phase effects is much bigger (~1000 times) than the term accounting for absorption, hence the dramatically increased sensitivity of PC.

There are three conventional ways of exploiting phase effects. One is to optimize the sample-to-detector distance and detect the interference pattern which results from the phase perturbations: this approach is called free-space propagation or in-line holography. The results provided by this approach are strongly dependent on the source characteristics, which make the results obtainable with conventional sources rather poor. Excellent images are obtained with synchrotron radiation, but in order to transfer the technique to conventional sources severe tradeoffs on image quality and/or exposure times have to be accepted.

Examples of this approach may be found in A. Snigirev et al, On the possibilities of x-ray phase contrast microimaging by coherent high-energy synchrotron radiation, Rev. Sci, Instrum. volume 66 (1995) pages 5486-92, and S. W. Wilkins et al Phase-contrast imaging using polychromatic hard x-rays, Nature volume 384 (1996) pages 335-8.

A second approach involves the use of interferometers. Traditionally these are obtained by proper cutting of perfect crystals, which leads to a number of problems—only very small fields of view can be observed, the required beam has to be strictly parallel and monochromatic, and the radiation dose is delivered ineffectively. This makes the approach very difficult to apply in most situations. An example of this approach is that described in A. Momose et al Phase-contrast x-ray computed tomography for observing biological soft tissues, Nature Medicine volume 2 (1996) pages 473-5.

Recently, an approach based on grating interferometers was devised, which solves some of the problems related to the use of conventional, crystal-based interferometers. This approach is described in F. Pfeiffer et al Phase retrieval and differential phase-contrast imaging with low-brilliance x-ray sources, Nature Physics 2 (2006) 258-61.

However, this approach has limitations also: the interferometers are obtained by sophisticated microfabrication techniques currently allowing a maximum field of view of 5-6 cm, dose is delivered ineffectively, the technique is sensitive to phase effects in one direction only, it is necessary to step the gratings in at least four different positions to acquire a single image, and the spectral bandwidth of the radiation beam must be smaller than 10%.

The third approach is based on the fact that the distortions of the x-ray wavefront due to phase shift result in local microvariations in the x-ray direction. In other words, after exiting the imaged sample, the direction of the x-rays has changed by a few tens of microradians, which is an effect that can be detected and translated into image contrast.

This is done using an analyzer crystal which, being characterized by a very narrow reflectivity curve, allows the translation of angular deviations into intensity differences. Examples of this approach are provided in V. N. Ingal and E. A. Beliaevskaya X-ray plane-wave topography observation of the phase contrast from a non-crystalline object, J. Phys. D: Appl. Phys. volume 28 (1995) pages 2314-7, and D. Chapman et al Diffraction enhanced x-ray imaging, Phys. Med. Biol. volume 42 (1997) pages 2015-25.

This allows a very flexible approach (the system sensitivity can be changed by changing the crystal orientation) resulting in extremely high image quality, in most cases higher than that provided by all other approaches mentioned here.

However, the necessity of relying on a perfect crystal strongly limits the third approach's applicability, for four main reasons:

1) The system requires monochromatic, parallel radiation. This makes it the perfect tool for imaging with synchrotron radiation, but makes it extremely ineffective when a commercial x-ray source is employed. The result is an increase in the exposure time of possibly two or more orders of magnitude.
2) The dose is delivered inefficiently. The crystal absorbs a considerable fraction of the x-rays after they have transversed the sample. Increased doses are of course a particular problem in medical applications.
3) The system is highly sensitive to environmental vibrations: a change of 1 microradian in the crystal orientation is enough to affect image quality
4) The system is intrinsically sensitive to phase effects in one direction only.

Thus, all three approaches have their disadvantages.

Another experimental approach uses synchrotron radiation, as described in A. Olivo et al An Innovative Digital Imaging Set-up Allowing a Low-Dose Approach to Phase Contrast Applications in the Medical Field, Med. Phys. volume 28 (2001) pages 1610-1619.

In these experiments it was observed that by illuminating with x-rays only the edge of the active surface of a line of pixels, it is possible to achieve a high sensitivity with respect to very small angular deviations in the photon direction.

Unfortunately, this experimental approach is difficult to convert to a commercial system for a number of reasons. Firstly, the approach inherently needs a flat x-ray sheet such as available from a synchrotron, and this is not available from conventional sources. The use of a synchrotron delivers highly collimated X-rays, and approaches using such radiation are difficult to convert to conventional sources for which beam divergence is a real issue. The use of a slit would greatly reduce the output x-ray intensity, making long exposure times necessary. Further, the approach does not work with conventional two-dimensional image detectors with an array of pixels which makes the approach incompatible with most existing equipment. Moreover, scanning across a sample to build up an image from a single line of detectors makes the process even slower and also makes it very difficult to maintain alignment. Such scanning is thus not compatible with commercial equipment where dosage limits and the timescale to record data are significant factors for example for use in medical or security applications.

The scientific community involved in x-ray imaging research fully agrees on the fact that phase contrast imaging can create a big change in x-ray imaging. To the best of the inventors' knowledge, up to now only two systems based on phase contrast imaging have been commercialized and they both suffer from limited applicability and/or limited improvements in image quality, for reasons discussed above.

Accordingly, there remains a need for an improved method of phase contrast imaging.

SUMMARY OF THE INVENTION

According to the invention there is described an x-ray imaging system as set out in claim 1.

The inventors have discovered that using an arrangement as set out in claim 1 allows the use of non-parallel x-ray beams and so avoids the need for expensive synchrotron sources. Instead, conventional commercial sources can be used.

Such commercial sources generally produce much less radiation than synchrotron sources, and the radiation is uncollimated.

In the invention described here, small variations in the x-ray direction are detected by means of a combination of a sample mask and pixel edges at the detector. In this way, image quality fully comparable to the one provided by the analyzer crystal-based approach is obtained while completely removing the four limitations outlined above:

1) The system uses diverging, fully polychromatic radiation, i.e. the kind of radiation provided by conventional sources.
2) The dose is delivered much more efficiently than in any other crystal or interferometric method. This will be discussed in more detail in the following section.
3) The system has negligible sensitivity to environmental vibrations.
4) Effective sensitivity to phase effects in both directions can be achieved with more than one possible slit design as discussed in more detail in the detailed description In another aspect, the invention relates to a method according to claim 11.

BRIEF DESCRIPTION OF THE DRAWINGS

For a better understanding, specific embodiments will now be described, purely by way of example, with reference to the accompanying drawings in which.

The figures are purely schematic and not to scale. Like or similar components are given the same reference numerals in different figures.

DETAILED DESCRIPTION

Figure 1:
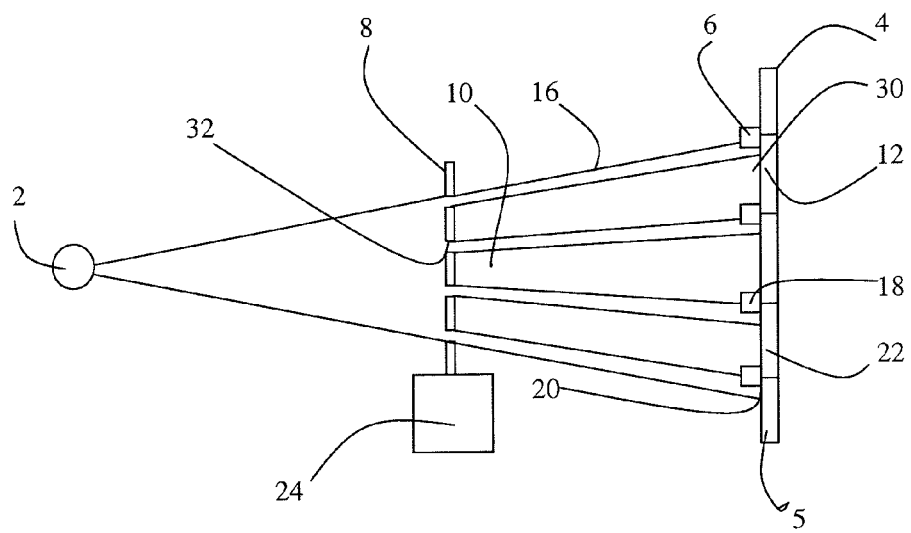
FIG. 1 shows a schematic of an embodiment of the invention without a sample.

Referring to FIG. 1, the system according to the first embodiment of the invention consists of an x-ray source 2, an x-ray detector 4 and a sample mask 8 placed immediately before the sample region 10. The x-ray source is not a synchrotron source, which would be inherently collimated and monochromatic, instead it is a conventional commercial source. For example, the source may be a molybdenum target source; many other commercial sources are available. Such sources are not in general monochromatic, instead although such sources frequently have a dominant energy they in fact emit small amounts of energy at other frequencies, and in this sense are polychromatic. Thus, in this specification, "polychromatic" is not intended to require a broad spectrum of frequencies. Further, such commercial sources are also not inherently collimated in the way that synchrotron sources are, instead X-rays are emitted in a range of angles; thus the emitted X-rays are both divergent and uncollimated.

Figure 9:
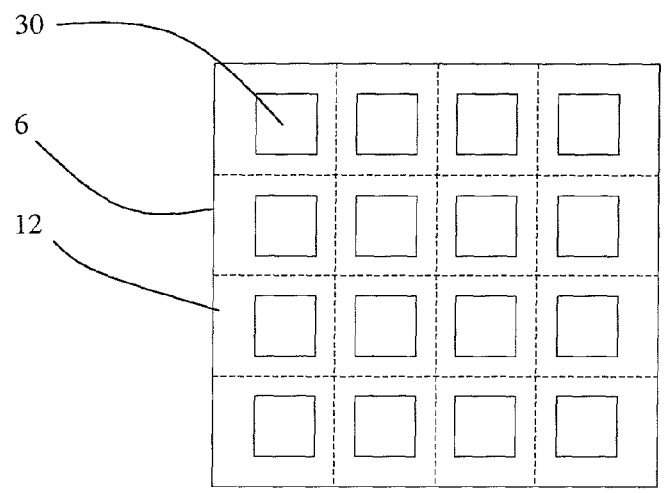
FIG. 9 shows a detector mask according to another embodiment.

The x-ray detector 4 is made up of a two-dimensional array 5 of pixels 12 in which the pixels extend to form rows and columns (not shown in this Figure—see FIG. 9). In the embodiment the detector includes a detector mask 6 defining pixel edges 20. The masks 6,8 are arranged to produce a specific shadowing effect in use, as will now be described. In particular, the detector mask 6 is arranged to have solid x-ray absorbing regions 18 over the boundaries between discrete pixels 12, defining an edge 20 between the x-ray absorbing regions 18 and apertures or slits 30. Each aperture 30 of the detector mask 6 thus defines the x-ray sensitive region, i.e. the uncovered area 22, of the corresponding pixel 12, since x-rays incident on the detector mask 6 are absorbed.

Apertures 32 are also provided in the sample mask 8.

Those skilled in the art will realise that depending on the source 2 used, additional beam-shaping optics or other matters may optionally be provided between the source 2 and the sample mask 8. However, in preferred embodiments such beam shaping is omitted and indeed it is a particular advantage of the invention that it works without any such beam-shaping.

When X-rays are emitted from the x-ray source 2 in the absence of a sample, the x-rays are transmitted in the beam direction and are absorbed by solid regions of the sample mask 8. Where the x-rays hit the apertures 32 in the sample mask they are transmitted as discrete beams 16 which fall on the detector mask 6. Each discrete beam 16 is arranged to fall partially on the x-ray absorbing region 18 and partially on the uncovered area 22 of the corresponding pixel 12, i.e. the discrete beam covers the edge 20. This means that only a certain fraction of the X-rays of each discrete beam 16 reach the uncovered area 22 of the pixel 12 and hence are measured.

Note that because of the divergent nature of the X-rays the pitch of apertures 32 in the sample mask 8 is smaller than the pitch of apertures 30 in detector mask 6.

Figure 2:
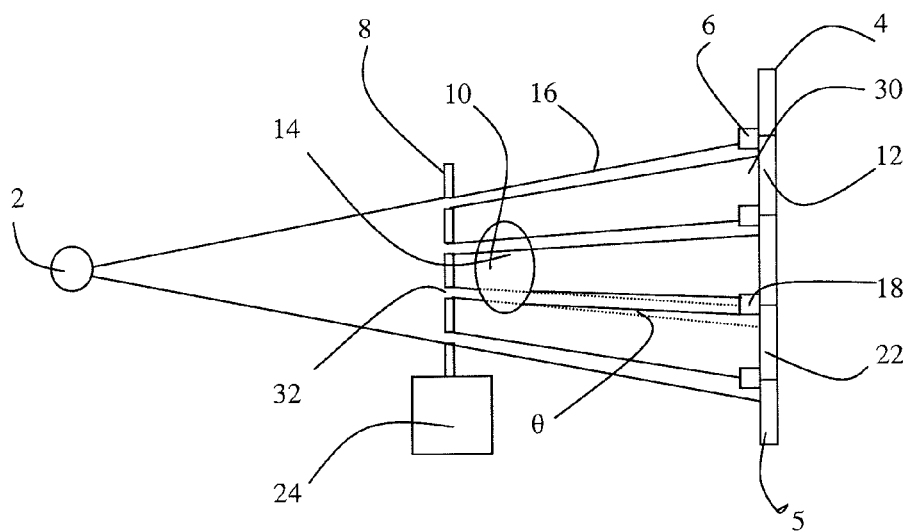
FIG. 2 shows the schematic of FIG. 1 with a sample added.

In use, as shown in FIG. 2, a sample 14 is placed in the sample region 10 and the discrete beams 16 are slightly deflected by angle θ as they pass through sample 14. The undeflected beam is shown dotted for comparison. The angle θ will be small—a small fraction of a radian—and is exaggerated in FIG. 2 for clarity. When this deflection is perpendicular to the edge 20 (up or down in FIG. 2, as shown) this slight deflection increases or decreases the fraction of X-rays of each discrete beam 16 which hits pixel 12, and hence affects the signal. This means that the detector can detect very small deviations of the discrete beams 16 caused by sample 14.

The exact arrangement of the sample mask 8 and the detector mask 6 can be arranged for good sensitivity.

In the preferred embodiment shown, the sample mask 8 is mounted on a two-dimensional micrometric positioning system 24. This allows the system to acquire images based on different techniques. The detector mask 6 may also be mounted on such a system.

Alternatively, the masks 6,8 may be mechanically held in place in the correct position.

It is important to notice that there is no need for any scan/stepping/movement of the masks 6,8 during image acquisition.

Note that the apertures 32 in the sample mask cause a plurality of x-ray beams 16 which hit the pixel edge of a respective plurality of rows of pixels, a respective plurality of columns of pixels or a respective plurality of individual pixels arranged in rows and columns. In this way, there are in effect multiple beams being used in parallel, which makes it possible to use lower intensity commercial x-ray sources without excessive measurement times.

The achieved image quality will depend on the size of the source 2. However, it is estimated that no relevant losses in image quality are expected for source sizes up to 50-70 microns. This is currently achievable with a wide range of commercial sources. Moreover, even in the case of a larger source size, image quality can be recovered by reducing the cross-section of the portion of the shaped beams which hits the pixel active surface. This can be done at a design stage, on the basis of the chosen source, or even after the system has been realized, by further shifting the pre-sample aperture system with respect to the detector one. This second solution, although much more flexible, has some cost in terms of delivered dose, which may be an issue in medical applications.

We now proceed with a more detailed discussion of the masks 6,8. Note that the invention can be used with either long slits—that is to say one-dimensional apertures—or individual apertures for each pixel, which will be referred to as two-dimensional apertures. The slits provide edge enhancement for edges oriented only along the direction of the slits, whereas the two-dimensional apertures provide edge enhancement regardless of the orientation of the edge. The terms one-dimensional and two-dimensional thus refer to the edge enhancement—both work with two-dimensional arrays of pixels as the detector that is to say conventional image arrays.

The description will start from the simplified one-dimensional case of a system sensitive to phase effects in one direction only. This will allow the clarification of a few basic points. Afterwards a few designs for two-dimensional exploitation of phase effects will be given.

In the simplest example the sample mask 8 and detector mask 6 are both formed of metal foil with horizontal (or vertical) slits 30,32 all across the metal foil, one for each pixel row (or column) in the detector. The pitch of the slits 30 in the detector mask 6 is determined by the pitch of the detector pixels 12, and the pitch of the slits 32 in the sample mask 8 is determined by the pitch of the detector pixels 12 multiplied by the source-to-sample distance and divided by the source-to-detector distance.

Figure 3:
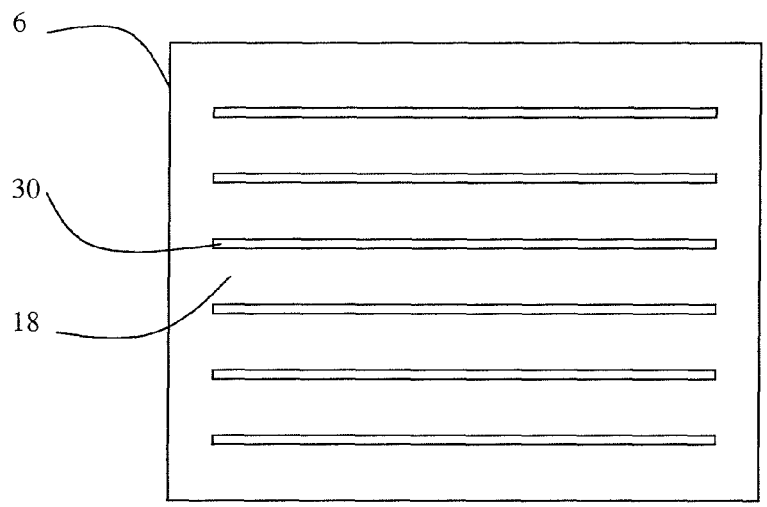
FIG. 3 shows a detector mask of the embodiment of FIG. 1.
Figure 4:
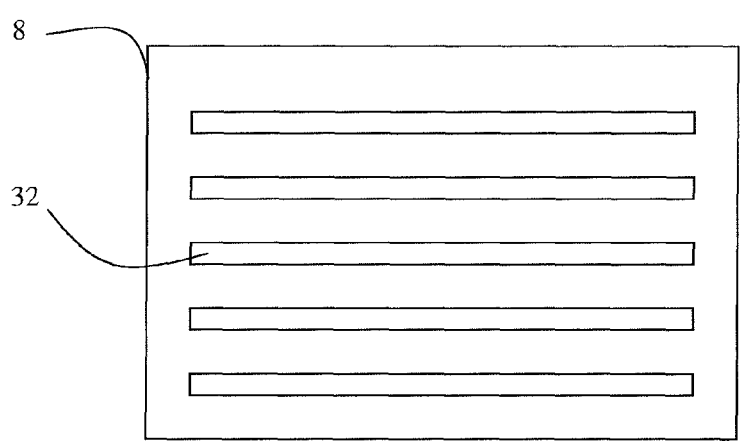
FIG. 4 shows a sample mask of the embodiment of FIG. 1.
Figure 5:
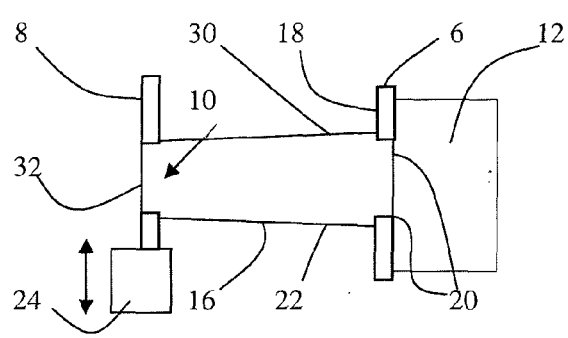
FIG. 5 shows a first schematic of an individual pixel and beam.

For what concerns the dimensions and locations of the slits 30, 32 three different approaches can be followed:

The first approach is illustrated in FIGS. 3 to 5. FIG. 3 shows the detector mask, FIG. 4 shows the sample mask and, FIG. 5 a schematic diagram of a single beam 16 hitting a single pixel 12.

The slits 32 in the sample mask 8 form discrete beams 16 of X-rays that fall across the slits 30 in the detector mask, spanning the full uncovered area 22 of pixel 12 and accordingly both edges 20 of the bars in the detector mask. In this arrangement, each pixel 12 has two pixel edges 20 defined by the edges 20 of the bars in the detector mask. The slits 30 in the detector mask 6 are fully illuminated by radiation, together with a slight fraction in the immediate vicinity of the aperture of the x-ray absorbing region 18 of the detector mask 6 between the slits 30.

If this approach is followed, the slits 30 in the detector mask 6 should be small, typically one third or one quarter of the detector pixel size, as the signal scales down with the size of these apertures. The slits 32 in the sample mask should be determined in such a way that the projected height of the beams reaching the detector is slightly larger (by a few microns on each side) than the apertures in the detector mask. This is easily achieved by simple ratio calculations after the source-to-sample and sample-to-detector distances have been chosen.

In a specific example, the pixel size is 254 µm, the source-to-sample distance is 1.6 m and the sample-to-detector distance is 0.4 m. In this case, the slits 30,32 in both sample and detector mask are 50 µm across, and have a pitch 254 µm in the detector mask 6 and 203 µm in the sample mask 8.

Figure 6:
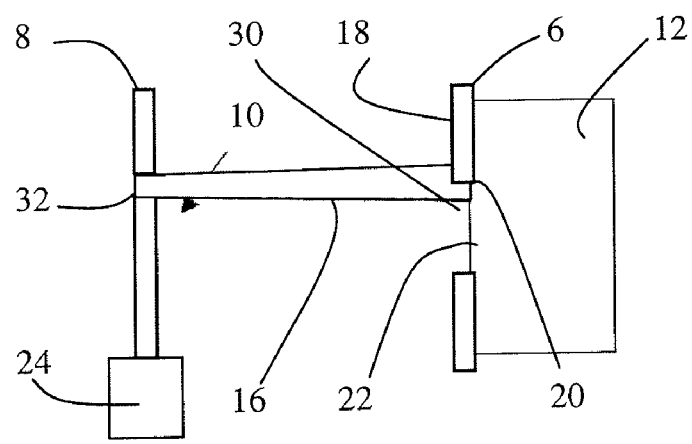
FIG. 6 shows a second schematic of an individual pixel and beam.

A second approach is shown in FIG. 6 and this appears at present to be the most effective as well as the simplest. FIG. 6 is a schematic showing the set-up in the region between sample and detector and the expected signal.

Figure 8:
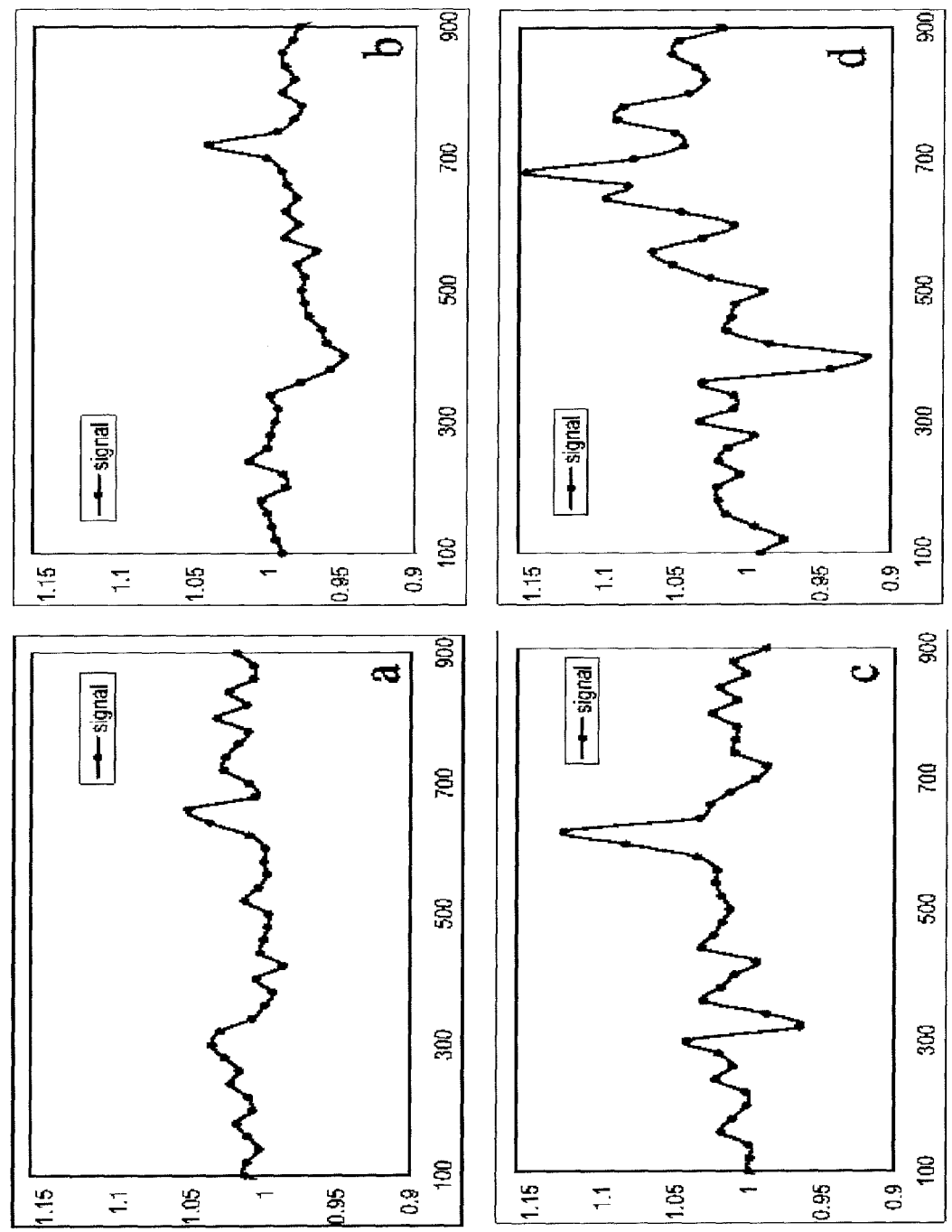
FIG. 8 illustrates preliminary results.

In this case, narrower slits 32 are used in the sample mask 8 defining beams directed at one edge 20 of the detector mask 6. Broader slits 30 than in the first approach are used in the detector mask 6. The results as shown in FIG. 8 show a much larger enhanced edge effect and this approach greatly improves the enhancement in contrast.

If this second approach is followed, the width of the slits 30 on the detector mask 6 has no influence on image quality as long as the width is smaller than the pixel size. The image quality is determined by the fraction of beam hitting the detector active surface. As a consequence, generally speaking the narrower the width of the slits 32 in the sample mask 8, the higher the image quality. This is something that can be determined beforehand on the basis of the flux provided by the x-ray source 2 and the limits on maximum exposure time.

However, if the sample mask 8 is mounted on a micrometric precision translation stage 24, the system has a degree of flexibility in the sense that it is possible to achieve an increase in image quality at the expense of a higher dose and/or exposure time by shifting the sample mask slightly upwards (from the position shown in FIG. 6). By doing this, a smaller portion of the pixel active surface, in the very vicinity of the end of the active surface itself, will be illuminated. This means that even the smaller angular deviation caused by the sample will make these photons contribute to the signal significantly. The results presented below (FIGS. 8b, 8c, 8d) show this effect.

Compared with the first approach, the second approach uses a lower dose and this may be important for some applications, especially medical applications.

It is important to notice that, in those cases in which the delivered dose is not an issue, the situation outlined in the present sub-section can be achieved also with the set-up described in the first approach (FIG. 5) provided that the sample mask is mounted on a micrometric translation stage 24 and that the height of the beam reaching the detector is smaller than the distance between two neighbouring apertures in the detector mask. To achieve this effect, the sample mask is moved as indicated by the arrows in FIG. 5 until the beam 16 mostly hits the x-ray absorbing region 18 between neighbouring slits 30 in the detector mask, only a small amount of x-rays reaching the uncovered area 22 of the detector pixel.

This results in a similar situation to the second approach using the mask of the first approach at the cost of a higher dose. This would be the optimal solution for a highly flexible system to be used in non-destructive testing or security inspections.

Figure 7:
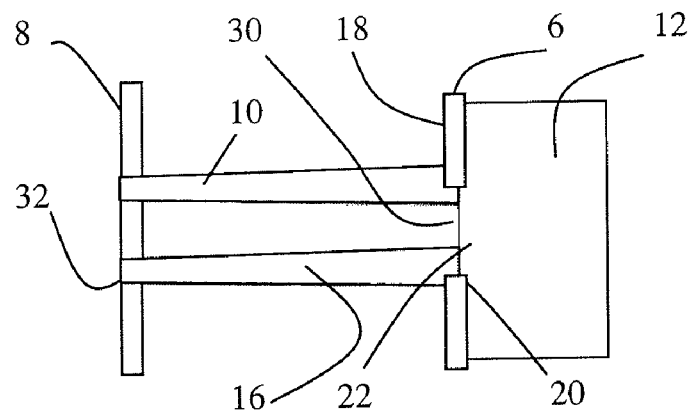
FIG. 7 shows a third schematic of an individual pixel and beam.

A third approach is illustrated in FIG. 7. This third approach combines to some extent the advantages of the first and second approach by providing for every slit 30 the detector mask 6 two slits 32 in the sample mask 8.

This approach allows the acquisition of free-space propagation-type signals with increased intensity with respect to first approach, as the central part of the beam hitting each pixel, which is the one that contributes less effectively to the signal, has been removed.

In the third approach of FIG. 7, as for the second approach of FIG. 6, the dimension of the slits 30 in the detector mask 6 has no influence on the signal intensity, which is determined by the fraction of beam hitting the pixel active surface, and consequently by the slits 32 in the sample mask 8. However, the system has less flexibility than the one described in the second approach, because moving the sample mask upward or downwards would result in increasing the signal due to one side of the pixel while decreasing the one due to the other side. Consequently the mask slit should be designed in advance according to the source power and desired exposure time, placed in the optimal position and left there. However, in some applications the possibility of having double positive/negative peaks in the acquired signal might result in an enhanced detectability of the details.

FIG. 8 illustrates measured results using the first approach of FIG. 5 in FIG. 8a and the second approach of FIG. 6 in FIGS. 8b, 8c, and 8d. It should be noted that these results are preliminary only and have been taken with very limited optimisation of the equipment. Nevertheless, the improvement using the invention can still be seen. FIG. 8a shows a horizontal profile extracted from an image of a polyethylene fiber using the arrangement of FIG. 5. The peak at around 700 arbitrary units is just visible at the limit of resolution.

FIGS. 8b, 8c and 8d correspond to the case of the second approach (FIG. 6), with varying overlaps between the x-ray beam and the pixel. FIG. 8b has the maximum overlap, FIG. 8d has the minimum overlap, and FIG. 8c is intermediate.

The great increase in the visibility of the edges of the fiber using the invention is readily apparent.

Further, the same apparatus can also be used for extremely small angle x-ray scattering experiments. In this case, the positioner 24 is used to ensure that the individual beams just miss the slits 30 in the detector aperture, i.e. in the absence of a sample x-rays are shielded from the pixels. The introduction of a sample in the sample region can then cause phase contrast effects that shift the beams 16 very slightly so that they are detected.

The above approaches to one-dimensional edge enhancement can also be applied to two-dimensional edge enhancement with different patterns of apertures which in this case are shaped apertures rather than slits.

The first thing to stress is that the considerations detailed for the one-dimensional case hold also for the two-dimensional case. As a consequence, it is sufficient here to give the mask drawings, as the way in which they should be used is the same discussed above, with clear extrapolation from the 1D to the 2D case.

As in the 1D case, the detector mask fulfils the task of making the boundaries of each single pixel insensitive to radiation. A schematic representation is given in FIG. 9, in which the white squares represent the apertures 30 in the detector mask and the dashed black lines represent the separation between the pixels 12 in the underlying detector 4.

Figure 10:
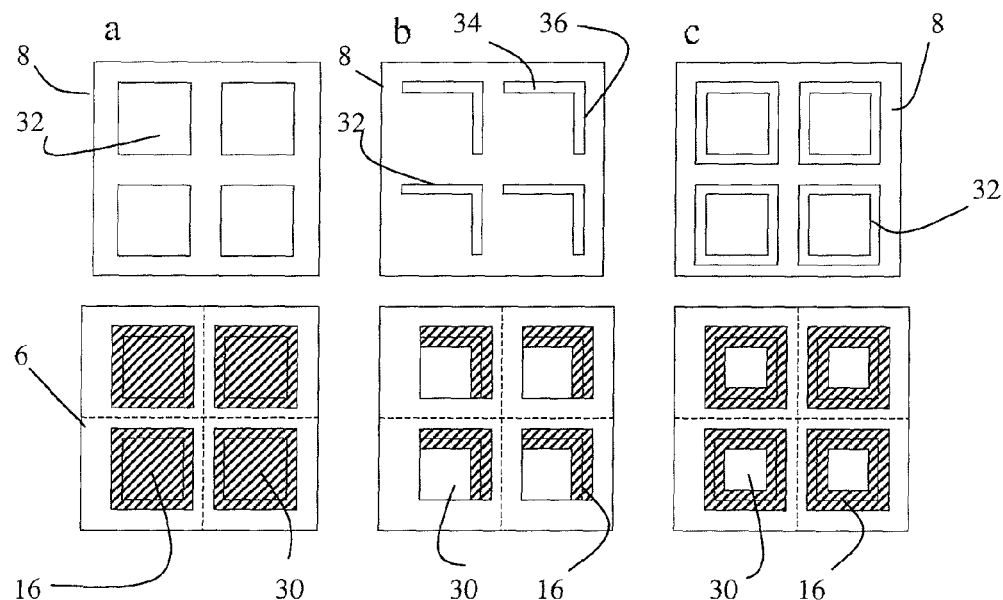
FIG. 10 shows sample and detector masks for alternative realisations of the FIG. 9 embodiment.

Different designs are used for the sample mask 8 to achieve the 2D equivalent of the different experimental conditions discussed above. These designs are displayed in FIG. 10 for the experimental conditions discussed in the first approach in FIG. 10a, the second approach in FIG. 10b and the third approach in FIG. 10c. Note in this case that there is a separate aperture 32 in the sample mask 8 for each pixel 12. In FIG. 10b, corresponding to the second 1d case, the aperture 32 is in the form of perpendicular slits 34,36 extending in the row and column directions.

The upper drawing in each case shows the sample mask 8 and the lower drawing shows a portion of the detector mask 6, including in particular the apertures 30 in the detector mask 6. The region where the corresponding individual beam 16 from the sample mask is incident on the detector mask 6 is shown using shading lines. As for the aperture dimensions, again the rules discussed in the 1D case hold also in the 2D one, with the appropriate proportion between source-to-detector and source-to-sample distance to be taken into account.

It should be noted that the masks 6,8 may also be made by thin metal foils, and in particular may be defined on a low-absorption substrate like graphite which is largely transparent to x-rays. Due to these low-absorption properties, it is not necessary to release the masks from the substrate in order to use them: this will allow also the structure shown in FIG. 8c to be realized with a central block in the aperture. Alternatively, thin metal strips might be left on the corners of each aperture to hold the central metallic squares in place.

An alternative that is particularly preferred is to integrate the detector mask 6 into the detector itself, manufacturing the mask 6 as a separate mask layer on top of the pixels during detector manufacture.

The same increase in sensitivity of the flexible system as discussed above in the one-dimensional case would be obtained in the 2D case by shifting the sample mask depicted in FIG. 8b further towards the top right corner, in order to reduce both in the horizontal and in the vertical directions the fraction of the pixel illuminated by x-rays.

The degree of flexibility of the system described in has already been discussed, alongside with the possibility of swapping between the first and second approaches using the same mask design in those cases in which the dose is not an issue.

Further developments will now be described. These developments can be used with any of the embodiments above.

Simulations were carried out to determine optimum system size, and in particular simulations were carried out, with 1.5 m between the source and the detector, and with 2 m. At each length, two different simulations were carried out, one with 50% of the pixel illuminated by radiation, and one with 25%.

Figure 11:
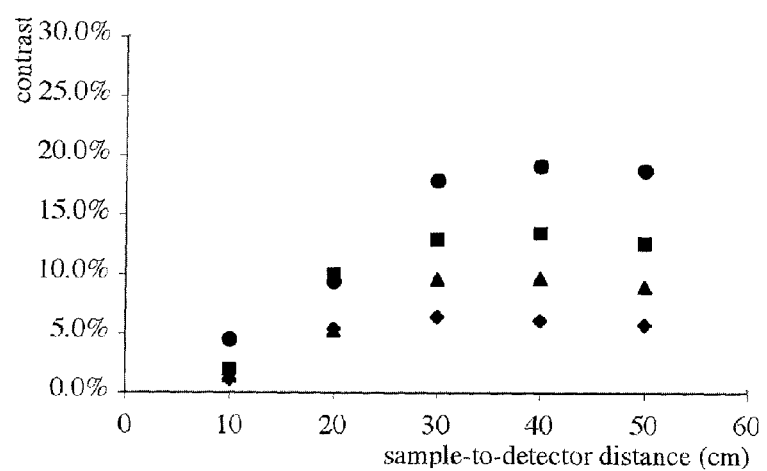
FIGS. 11 and 12 illustrate results obtained with embodiments in various configurations.

FIG. 11 illustrates the contrast as a function of sample-detector difference for these four cases.

All other things being equal, the longer system gives better results. However, the 1.5 m system with 33% illumination gives better results than the 2 m system with 50% illumination, i.e. the amount of illumination is more important than system length. Moreover, because of the smaller distance between source and detector, the X-ray intensity in the smaller system is greater by virtue of the inverse square law. Thus, a 1.5 m system also improves exposure time.

The initial experiments were carried out using 130 µm thick gold masks as the sample and detector masks. Such masks give 99% x-ray absorption up to 35 keV, and thus absorb almost all the energy from the Mo source used with a 17 keV mean energy.

However, such thick films cause difficulties, including cost and the effects of the finite thickness.

Accordingly, the effect of using gold thicknesses of 20 µm and 30 µm was investigated. Such films stop 99% of x-rays at 17 keV and 20 keV respectively, and thus let significant quantities of x-rays through, since the sources used are not monochromatic. In view of the polychromatic nature of the X-ray source, a suitable measure of mask absorption (the inverse of transparency) is the percentage of absorption of the X-rays emitted by the source. The 20 µm and 30 µm gold films let approximately 94% (20 µm) and 97% (30 µm) respectively of X-rays emitted from a Mo source.

Figure 12:
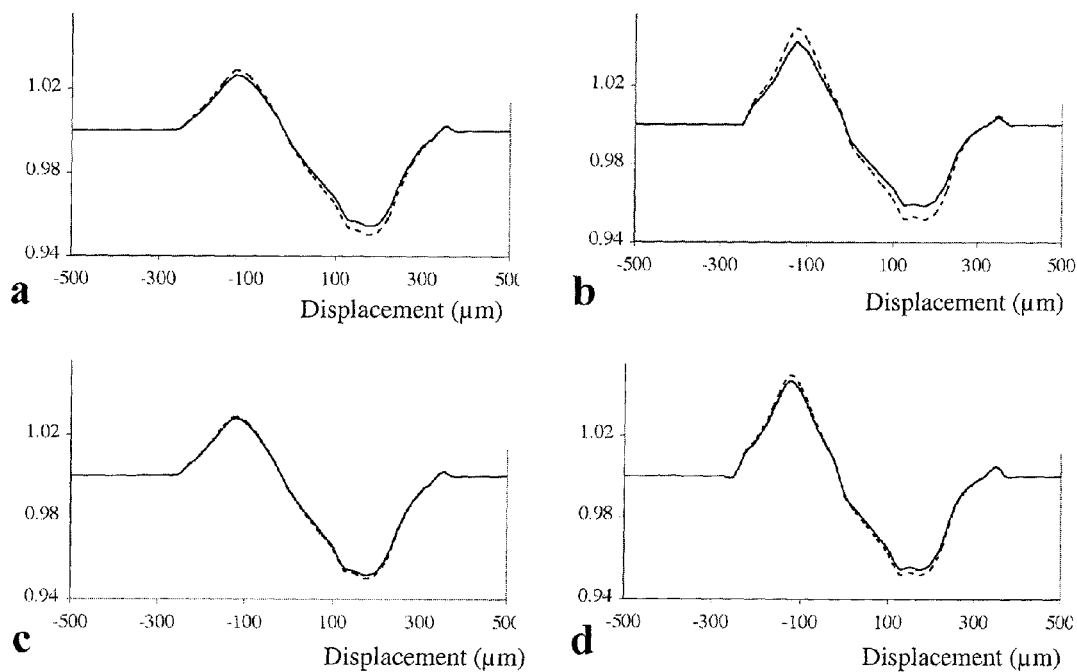

FIG. 12 illustrates the results compared with 130 µm thick gold. Graph a is for a 20 µm thick mask with 50% pixel illumination, graph b for a 20 µm thick mask with 33% pixel illumination, graph c for a 30 µm thick mask with 50% pixel illumination, and graph d for a 30 µm thick mask with 33% pixel illumination. Even with significant transmission through the masks good results are seen.

In embodiments, the sample and detector masks absorb less than 99.5%, for example 90% up to 99.5%, or even 92% to 99% or 93% to 98% of the total x-rays emitted by the x-ray source, to allow the mask to be thin.

For example, the sample and detector mask may be made of gold 10 to 300 µm thick, for example 15 to 70 µm thick. Those skilled in the art will realise that the material and thickness of the detector mask may be varied depending on the X-ray energy distribution of the chosen source.

Figure 13:
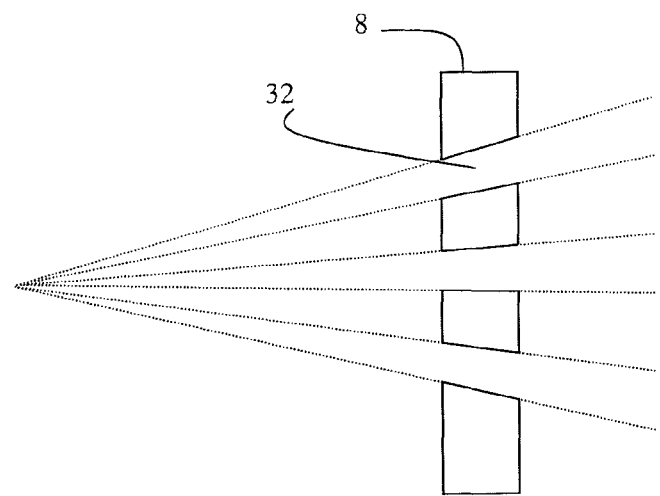
FIGS. 13 illustrates a further embodiment of the invention.

Another way of dealing with finite thickness masks is to shape the aperture edges of both sample 8 and detector 6 masks to deal with the fact that the x-rays are not parallel, particularly where thicker masks are used. FIG. 13 illustrates the angled aperture 32 edges of a sample mask 8, angled to be parallel to the primary x-rays. Since the x-rays are divergent, the edges are angled away from the centre of the mask in the direction of beam travel. A corresponding approach can be used for the detector mask.

Figure 14:
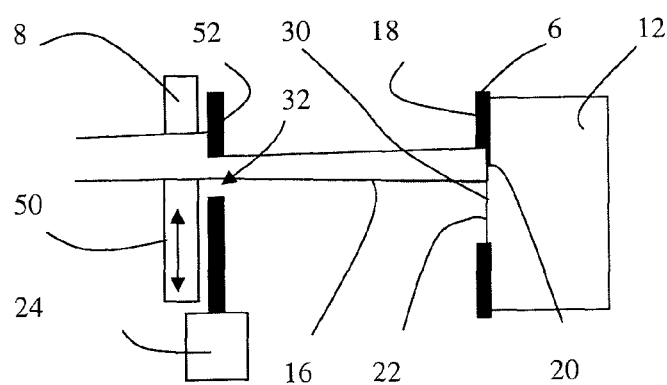
FIG. 14 illustrates a further embodiment of the invention.

A further development is illustrated in FIG. 14. In this case, the sample mask 8 made up of two parts, a first mask element 50 and a second mask element 52, arranged close together but moveable relative to one another in the plane of the mask. The apertures 32 in sample mask 8 have an effective size which can be adjusted by moving the first mask element 50 relative to the second mask element 52. This can be of particular use in reducing the intensity of the X-rays used, since a reduced aperture 32 size will result in a reduced dose. Thus, this approach can be used in dose-sensitive applications such as medical applications.

Figure 15:
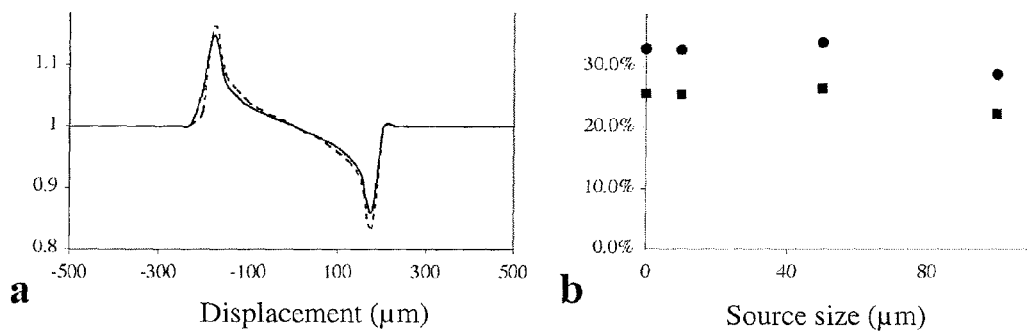
FIGS. 15 and 16 illustrate results obtained with embodiments of the inventions.

FIG. 15 illustrates the effect of a finite source size, as observed with commercial X-ray sources. The contrast as a function of source size is shown. Up to 50 µm no effect is seen, and only minor effects are seen at 100 µm. This demonstrates that the approach adopted works with finite sized sources.

Figure 16:
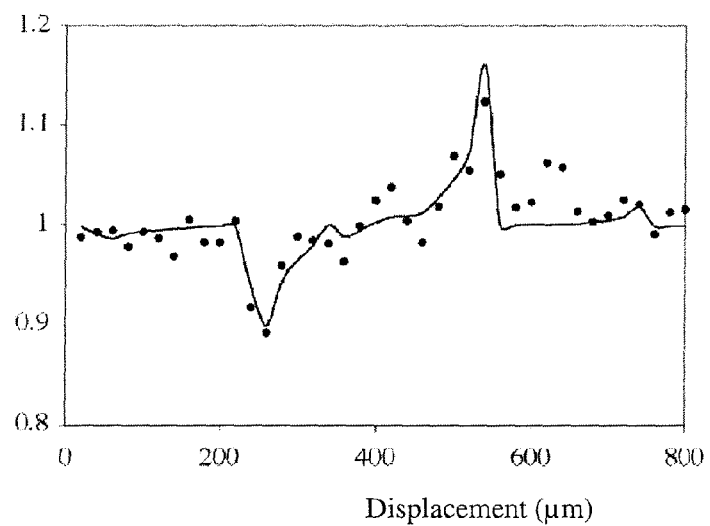

FIG. 16 illustrates actual results measured across an image of a 300 µm thick polyethylene fibre, including the actual measured intensity compared with a simulated profile. The good agreement validates those simulations used above.

Although the apparatus is specially designed for PC measurements, it is not limited to only carrying out PC measurements. The system would allow extremely small angle scatter imaging. This technique explores an angular region below 1°, perhaps below 0.2° or even 0.1° which is far below the angles used in conventional small angle scattering of perhaps 2° to 5°. Swapping from PC to extremely small angle scatter imaging would easily be obtained with the set-up shown in FIG. 7, by simply shifting the sample mask upwards in such a way that the shaped beams would not hit the detector active areas. This provides the system with another relevant degree of flexibility.

Moreover, by using different pitches for the odd and even lines (or columns) of apertures in the sample mask, in such a way that subsequent lines (columns) of shaped beams would alternatively hit/miss the pixel active surface, it would be conceivable to acquire PC and scatter images at the same time. Obviously, the scatter and PC images obtained in this way would be characterized by a spatial sampling frequency reduced by a factor of two, but possible solutions to this problem could be obtained by dithering techniques (i.e. acquiring two different images by shifting the sample or the imaging apparatus in between) or by using detectors with double resolution with respect to the original requirements.

In general, it is important to notice that, since the proposed technique requires a reduction of the pixel active surface, it results in an increase of the intrinsic resolution of the used detector. As a consequence, dithering techniques would provide in this case higher benefits with respect to the ones they provide in other techniques.

It should be noted however that the invention does not require any particular post processing algorithm, since the improved results can simply be seen in the recorded image.

The only limit of the technique is that it relies on the physical separation between neighbouring detector pixels, i.e. x-rays counted by one pixel ideally should not influence the number of counts recorded by the neighbouring one. For some detectors, notably indirect conversion systems employing non-structured scintillators, this is not the case. Hence the technique works at its full potential when direct conversion detectors are employed, and almost optimal results can be obtained with indirect conversion system employing structured scintillators. In this last case, moreover, the fact that the technique requires the pixels to be illuminated only in their central part is of great help in limiting the number of counts that might be induced in neighbouring pixels.

In general, the effect of inducing counts on neighbouring pixels is a loss in image contrast. This loss, however, is practically negligible for an induced number of counts kept within 10-15% of the total counts in the illuminated pixel. This condition is easily achieved in both situations mentioned above.

However, the technique could be used also with indirect detectors employing non-structured scintillator by designing a sample mask illuminating only half the pixels in a "chessboard" fashion. The loss in resolution could then be recovered by dithering techniques. Alternatively, for some applications a loss in the contrast might be accepted and/or partly compensated by reducing the illuminated area on the pixel as described above. It should however be noted that the invention uses relatively sharp transitions (i.e. the edges) and some conventional devices with insensitive regions (known as a limited fill factor) have smooth transitions between sensitive and insensitive regions. For such detectors, the use of a mask is advantageous to achieve sharp edges.

Note also that although all the embodiments described above use a separate detector mask 6 on the top of the pixel array 5, the invention can in principle be used with a detector 4 in which the pixel edges are part of the pixel array 5 itself, for example as a result of the edges of individual pixels 22 in the detector. Such an approach aids accurate registration of mask to pixels. Alternatively, a wholly separate metal mask 6 may be used, this latter case allowing the metal mask to be mounted on a micropositioner for adjustment.

Although the description uses rows and columns the directions of these rows and columns is essentially arbitrary and the use of the term "row" should not be thought of as implying the need for the row to be horizontal—the rows and columns may be horizontal or vertical as required.

Further, in some embodiments, the pixels may be arranged in rows but not in columns, the pixels in adjacent rows being offset from one another The shape of the pixels and the detector mask may be varied as required. For example, the pixels and apertures may be square, rectangular, or any shape giving the required results.

The invention claimed is:

1. An apparatus for phase contrast x-ray imaging a sample in a sample region (10), comprising:
   a source (2) of x-rays;
   a sample mask (8) between the source of x-rays and the sample region (10), the sample mask including a plurality of apertures (32) for defining a respective plurality of individual x-ray beams (16); and
   an x-ray detector (4) with a plurality of detector pixels (12) having sensitive regions sensitive to x-rays and insensitive regions insensitive to x-rays, the sensitive regions being bounded from the insensitive regions by pixel edges;
   wherein:
   the pixels (12) are arranged as a two dimensional array (5) of pixels arranged in rows;
   the source (2) of x-rays is a polychromatic, uncollimated source of x-rays; and
   the apertures (32) in the sample mask are arranged such that the x-ray beams (16) pass through the sample region (10) and hit the pixel edges of a plurality of rows of pixels corresponding to the plurality of x-ray beams, a plurality of columns of pixels corresponding to the plurality of x-ray beams or a plurality of individual pixels corresponding to the plurality of x-ray beams.

2. An apparatus according to claim 1 wherein the sample mask (8) defines a two dimensional array of apertures matching the pattern of pixels of the x-ray detector, each aperture corresponding to a respective individual pixel of the x-ray detector.

3. An apparatus according to claim 2 wherein each respective aperture (32) in the sample mask (8) is a square oriented along the row and column directions arranged such that the individual x-ray beam generated by each respective aperture covers the whole of the sensitive region of the respective individual pixel and the insensitive region around the sensitive region.

4. An apparatus according to claim 2 wherein each respective aperture (32) in the sample mask (8) includes a slit (34) extending in the row direction and a slit (36) extending in the column direction arranged such that the individual x-ray beam generated by the respective aperture covers exactly two adjacent pixel edges extending in the row and column direction of the respective pixel.

5. An apparatus according to claim 1 wherein the x-ray detector includes a detector mask (6) facing the sample region, wherein the detector mask has a plurality of apertures (30) defining the sensitive regions of the pixels surrounded by solid regions defining the insensitive regions.

6. An apparatus according to claim 5 wherein the sample and detector masks (8,6) absorb up to 99.5% of the x-rays of the predetermined mean energy.

7. An apparatus according to claim 5 wherein the sample and detector masks (8,6) are made of gold 10 to 300 µm thick.

8. An apparatus according to claim 1 wherein at least some of the apertures (30,32) have angled edges arranged so that the angled edges are parallel to the x-rays emitted by the source passing through the respective apertures.

9. An apparatus according to claim 1 wherein the sample mask (8) comprises a first mask element (50) including a plurality of first apertures, and a second mask element (52) including a plurality of second apertures, wherein the first and second mask elements can be moved relative to one another to adjust the effective size of the apertures of the sample mask.

10. An apparatus according to claim 1, wherein the sample mask (8) defines a plurality of slits corresponding to respective rows of pixels, each slit extending in the row direction.

11. An apparatus according to claim 10 wherein each respective slit in the sample mask is arranged to generate an individual x-ray beam extending across a single pixel edge extending in the row direction of the pixels in the respective row.

12. An apparatus according to claim 10 wherein the sample mask (8) defines two slits for each row of pixels, the two slits arranged to generate a pair of individual x-ray beams corresponding to the opposed pixel edges extending in the row direction of each row of pixels.

13. An apparatus according to claim 1 further comprising a positioner (24) on which the sample mask is mounted for adjusting the position of the sample mask in the row and/or the column direction.

14. A method of phase contrast x-ray imaging comprising:
   generating polychromatic, uncollimated x-rays from an x-ray source (2);
   illuminating a sample mask (8) having a plurality of apertures (32) with x-rays to generate a plurality of individual x-ray beams (16); and
   passing the plurality of individual x-ray beams (16) through a sample (14) to an x-ray detector (4) wherein the x-ray detector has a plurality of detector pixels (12) arranged as a two dimensional array (5) of pixels having rows of pixels, the pixels having sensitive regions sensitive to x-rays and insensitive regions insensitive to x-rays, the sensitive regions being bounded from the insensitive regions by pixel edges;
   wherein the apertures (32) in the sample mask are arranged such that the x-ray beams hit the pixel edges of a plurality of rows of pixels corresponding to the plurality of x-ray beams, a plurality of columns of pixels corresponding to the plurality of x-ray beams or a plurality of individual pixels corresponding to the plurality of x-ray beams.

15. A method according to claim 14 wherein the sample mask (8) defines a two dimensional array of apertures (32) matching the pattern of pixels of the x-ray detector, each aperture corresponding to a respective individual pixel of the x-ray detector, the method including aligning the sample mask so that the respective apertures define individual x-ray beams hitting the respective pixels.

16. An method according to claim 15 wherein each respective aperture in the sample mask (8) includes a slit (34) extending in the row direction and a slit (36) extending in the column direction, the method including arranging the sample mask such that the individual x-ray beam generated by the respective aperture covers exactly two adjacent pixel edges extending in the row and column direction of the respective pixel.

17. A method according to claim 14, wherein the sample mask (8) defines a plurality of slits corresponding to respective rows of pixels, each slit extending in the row direction, the method including arranging the sample mask such that the individual x-ray beam generated by the respective slits each extend across at least one pixel edge extending in the row direction of the pixels in the respective row.

18. A method according to claim 14 further comprising a detector mask (6) at the ray detector (4), the detector mask (6) facing the sample region having a plurality of apertures defining the sensitive regions of the pixels surrounded by solid regions defining the insensitive regions, the method including arranging the detector mask (6) so that the plurality of apertures of the detector mask are aligned with the pixels (12).

19. A method according to claim 18 wherein the sample and detector masks (6,8) absorb up to 99.5% of the x-rays emitted by the source.

20. A method according to any of claims 14 further comprising adjusting the position of the sample mask (8) in the row and column directions to align the individual x-ray beams (16) with the pixels (12) of the detector.

21. A method according to claim 14 wherein the sample mask comprises a first mask element (50) including a plurality of first apertures, and a second mask element (52) including a plurality of second apertures, the method including moving the first mask element (50) relative to the second mask element (52) to adjust the effective size of the apertures of the sample mask.

* * * * *